(12) United States Patent
Nakasone et al.

(10) Patent No.: US 10,241,074 B2
(45) Date of Patent: Mar. 26, 2019

(54) GAS SENSOR

(71) Applicant: NGK INSULATORS, LTD., Nagoya-shi, Aichi (JP)

(72) Inventors: Osamu Nakasone, Inabe (JP); Takayuki Sakurai, Kakamigahara (JP); Satoshi Nishikawa, Chita (JP); Noriko Hirata, Nagoya (JP); Yuki Nakayama, Nagoya (JP)

(73) Assignee: NGK INSULATORS, LTD., Nagoya (JP)

( * ) Notice: Subject to any disclaimer, the term of this patent is extended or adjusted under 35 U.S.C. 154(b) by 555 days.

(21) Appl. No.: 14/823,217

(22) Filed: Aug. 11, 2015

(65) Prior Publication Data

US 2016/0061768 A1 Mar. 3, 2016

(30) Foreign Application Priority Data

Aug. 29, 2014 (JP) ................................. 2014-176043

(51) Int. Cl.
*G01N 27/407* (2006.01)
*G01N 27/419* (2006.01)
(Continued)

(52) U.S. Cl.
CPC ....... *G01N 27/4074* (2013.01); *G01N 27/301* (2013.01); *G01N 27/4072* (2013.01); *G01N 27/41* (2013.01); *G01N 27/419* (2013.01)

(58) Field of Classification Search
CPC .......... G01N 27/406; G01N 27/407–27/4078; G01N 27/409; G01N 27/41; G01N 1/2247–1/2258; G01M 15/10–15/108; B01D 53/32–53/326; Y02T 10/47; F01N 11/007; F01N 2560/026
See application file for complete search history.

(56) References Cited

U.S. PATENT DOCUMENTS 6,076,393 A * 6/2000 Kato ................... G01N 27/4074
204/425
6,153,072 A 11/2000 Inoue et al.
(Continued)

FOREIGN PATENT DOCUMENTS

JP 2002-540400 A 11/2002
JP 3566089 B2 6/2004

*Primary Examiner* — Maris R Kessel
(74) *Attorney, Agent, or Firm* — Global IP Counselors, LLP

(57) ABSTRACT

Provided is a gas sensor having excellent detection sensitivity and responsiveness. In a sensor element, 3.5≤D2/D1≤6 is satisfied, where D1 is a value of a diffusion resistance of a measurement gas via a main gas distribution part extending from an outside edge position of a first gas inlet to the second internal space, and D2 is a value of a diffusion resistance of a measurement gas flowing via a second gas inlet that causes the outside and the second internal space to communicate with each other. The concentration of a predetermined gas component contained in the measurement gas through the second gas inlet is determined on the basis of a potential difference between the sensing electrode and a reference electrode, while pumping oxygen in or out for the measurement gas via the main gas distribution part such that the oxygen concentration of the second internal space is maintained at 1 vol % or more.

16 Claims, 10 Drawing Sheets

(51) Int. Cl.
G01N 27/30 (2006.01)
G01N 27/41 (2006.01)

(56) References Cited

U.S. PATENT DOCUMENTS

| | | | | |
|---|---|---|---|---|
| 6,554,983 B2 * | 4/2003 | Imamura | ............... | G01N 27/419 |
| | | | | 204/425 |
| 6,645,361 B1 | 11/2003 | Bloemer et al. | | |
| 2009/0229978 A1 * | 9/2009 | Mizutani | .............. | G01N 27/407 |
| | | | | 204/424 |
| 2009/0242404 A1 * | 10/2009 | Miyashita | .......... | G01N 27/4071 |
| | | | | 204/431 |
| 2011/0147214 A1 * | 6/2011 | Fujita | ................ | G01N 27/4071 |
| | | | | 204/424 |

* cited by examiner

F I G . 4
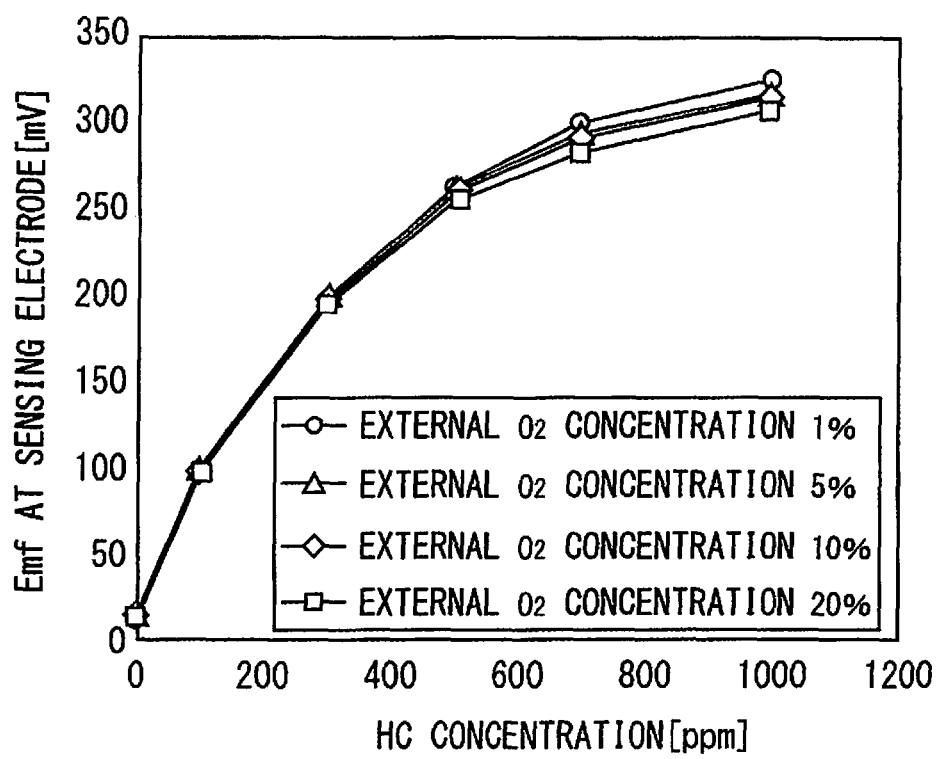

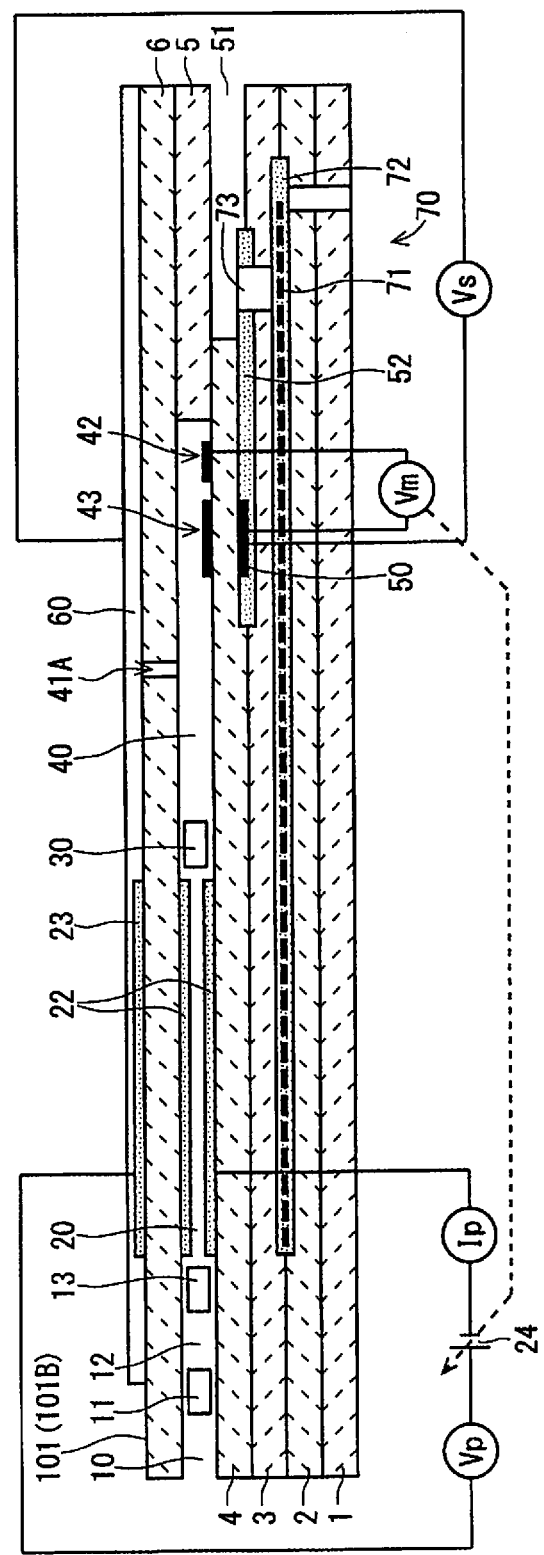

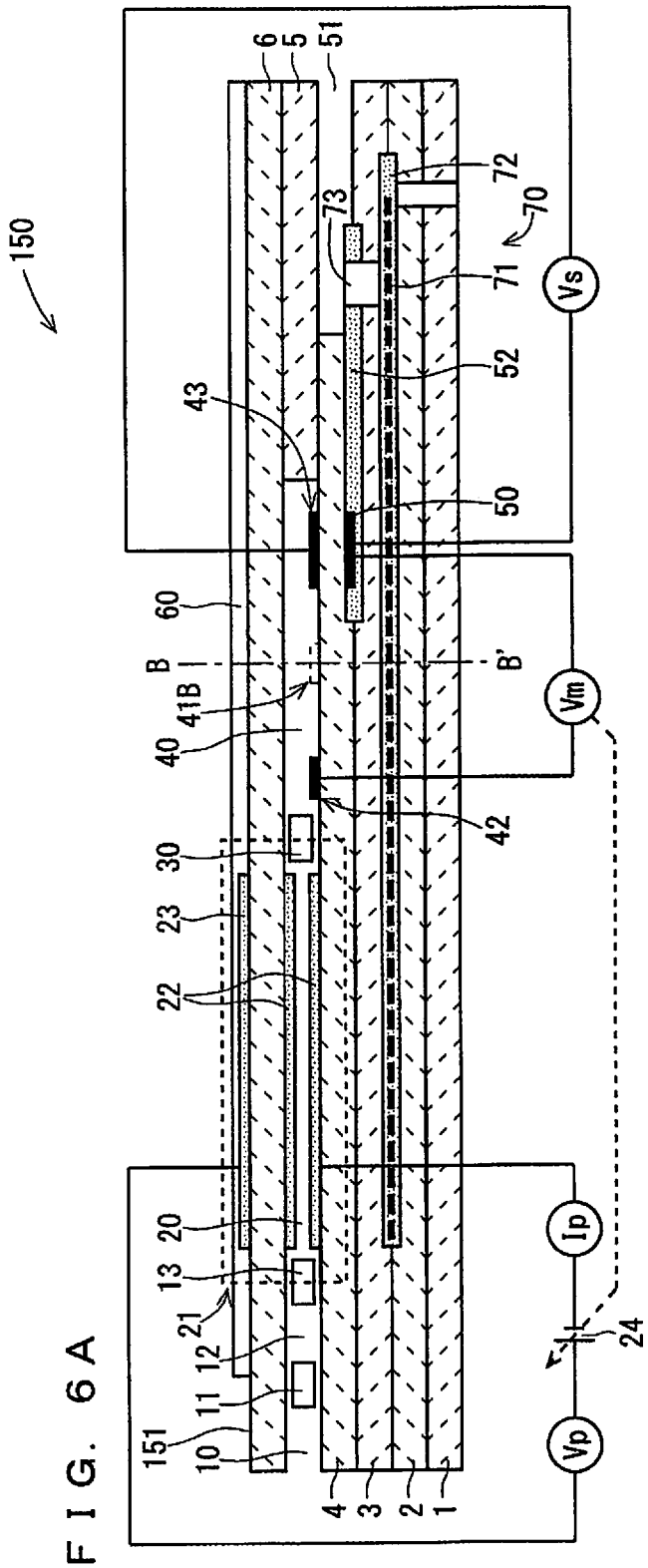
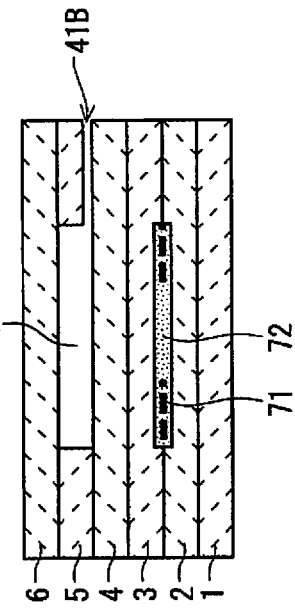
FIG. 6A
FIG. 6B

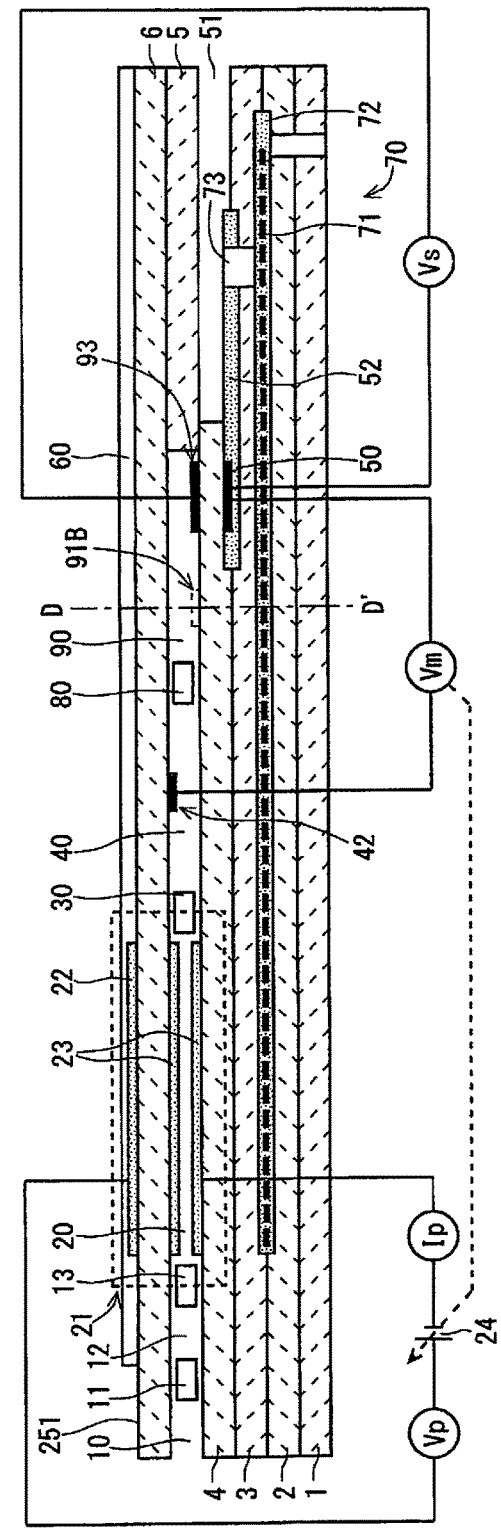
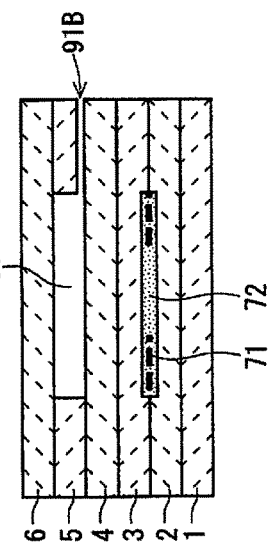
FIG. 8A
FIG. 8B

GAS SENSOR

BACKGROUND OF THE INVENTION

Field of the Invention

The present invention relates to a gas sensor that determines the concentration of a predetermined gas component such as a hydrocarbon gas in, for example, a measurement gas being an exhaust gas from a diesel engine.

Description of the Background Art

Gas sensors that sense a predetermined gas component in a measurement gas and determine its concentration come in various types. For example, a limiting current gas sensor and a mixed-potential gas sensor are well known (for example, see Japanese Patent No. 3566089 and Japanese translation of PCT international application publication No. 2002-540400).

Japanese Patent No. 3566089 discloses a limiting current gas sensor having a two-chamber structure including a first processing chamber into which a measurement gas is introduced through a first gas distribution part and a second processing chamber into which the gas of the first processing chamber is introduced through a second gas distribution part. The gas sensor is configured to adjust the concentration of oxygen (in practice, oxygen partial pressure) in the first processing chamber to a predetermined range ($10^{-12}$ atm to $10^{-6}$ atm) that causes substantially no decomposition reaction of water vapor contained in the measurement gas and to determine the concentration of an inflammable gas component of the gas introduced into the second processing chamber on the basis of an amount of oxygen which is consumed when the inflammable gas component is burned. The gas sensor thus has the accuracy of sensing an inflammable gas, which is hardly affected by the decomposition of water vapor, and also can suitably operate in the lean-burn conditions.

Japanese translation of PCT international application publication No. 2002-540400 discloses a gas sensor including a sensor element, which can be used as a NOx sensor as well as a hydrocarbon (HC) sensor. The gas sensor includes a first measurement gas chamber provided with a first internal electrode catalytically inactive and a second internal electrode catalytically active, which is in contact with a measurement gas, a second measurement gas chamber separated from the first measurement gas chamber by an oxygen ion permeable layer, and a reference channel into which the air is introduced. The oxygen ion permeable layer includes a connection channel connecting the first measurement gas chamber and the second measurement gas chamber. Such a gas sensor conceivably functions as a mixed-potential gas sensor when used as an HC sensor.

In response to more stringent regulations on exhaust gas, there have recently been increasing demands for a diagnosis of failure in the performance of cleaning unburned hydrocarbon in an exhaust emission control system (TWC: three-way catalyst) of a gasoline engine and a diagnosis of failure in the performance of cleaning unburned hydrocarbon in an exhaust emission control system (DOC: diesel oxidation catalyst) of a diesel engine. These diagnoses require a gas sensor capable of sensing an unburned hydrocarbon gas and identifying its concentration.

For the gas sensor disclosed in Japanese Patent No. 3566089, a measurement gas having the lean composition, whose oxygen concentration has been reduced through oxygen pumping in the first processing chamber, is caused to have a stoichiometric composition or a somewhat rich composition and is then introduced into the second processing chamber. Although Japanese Patent No. 3566089 describes that such a configuration increases an output of the electromotive force of a concentration cell and also provides good sensitivity of the gas sensor, it involves such a problem that varying oxygen concentrations greatly affect the electromotive force of the concentration cell in the neighborhood of stoichiometric composition.

The gas sensor disclosed in Japanese translation of PCT international application publication No. 2002-540400 involves, for example, the following problems: because of its structure, errors tend to occur in reference oxygen concentration and control responsiveness of oxygen concentration becomes poor, and the positional relationship between a heater and each electrode does not reflect a temperature suitable for the operation of each electrode. Besides, Japanese translation of PCT international application publication No. 2002-540400 does not specifically describe how to control an oxygen concentration when the gas sensor is used as an HC sensor.

SUMMARY OF THE INVENTION

The present invention relates to a gas sensor that determines the concentration of a predetermined gas component such as a hydrocarbon gas, which is present in, for example, a measurement gas being an exhaust gas from a diesel engine. In particular, the present invention is directed to the structure of a mixed-potential gas sensor that includes a sensor element formed of an oxygen-ion conductive solid electrolyte and measures the concentration of the predetermined gas component in the measurement gas.

In an aspect of the present invention, the sensor element of the gas sensor includes: a first gas inlet communicating with the outside; a first internal space communicating with the first gas inlet via a predetermined diffusion control part; a second internal space communicating with the first internal space via another predetermined diffusion control part; a second gas inlet causing the outside and the second internal space to communicate with each other; a sensing electrode located in the second internal space; a reference gas introduction space into which a reference gas is introduced; a reference electrode located in the reference gas introduction space; an oxygen pumping cell including an inside pump electrode facing the first internal space, an outside pump electrode located on an outside surface of the sensor element, and the solid electrolyte located between the inside pump electrode and the outside pump electrode; and a main gas distribution part being a path extending from the first gas inlet to the second internal space. The gas sensor is configured and disposed so as to determine the concentration of the predetermined gas component contained in the measurement gas introduced from the second gas inlet into the second internal space on the basis of a potential difference between the sensing electrode and the reference electrode, while causing the oxygen pumping cell to pump oxygen in or out for the measurement gas flowing via the main gas distribution part such that an oxygen concentration of the second internal space is maintained at a constant value of 1 vol % or more. In the gas sensor, $3.5 \leq D2/D1 \leq 6$ is satisfied, where D1 is a value of a diffusion resistance of the measurement gas flowing from an outside edge position of the first gas inlet to the sensing electrode via the main gas distribution part, and D2 is a value of a diffusion resistance of the measurement gas flowing from an outside edge position of the second gas inlet to the sensing electrode.

In another aspect of the present invention, the sensor element of the gas sensor includes: a first gas inlet communicating with the outside; a first internal space communicating with the first gas inlet via a predetermined diffusion control part; a second internal space communicating with the first internal space via another predetermined diffusion control part; a third internal space communicating with the second internal space via still another predetermined diffusion control part; a second gas inlet causing the outside and the third internal space to communicate with each other; a sensing electrode located in the third internal space; a reference gas introduction space into which a reference gas is introduced; a reference electrode located in the reference gas introduction space; an oxygen pumping cell including an inside pump electrode facing the first internal space, an outside pump electrode located on an outside surface of the sensor element, and the solid electrolyte located between the inside pump electrode and the outside pump electrode; and a main gas distribution part being a path extending from the first gas inlet to the third internal space. The gas sensor is configured and disposed so as to determine the concentration of the predetermined gas component contained in the measurement gas introduced from the second gas inlet into the third internal space on the basis of a potential difference between the sensing electrode and the reference electrode, while causing the oxygen pumping cell to pump oxygen in or out for the measurement gas flowing via the main gas distribution part such that an oxygen concentration of the second internal space is maintained at a constant value of 1 vol % or more. In the sensor element, $3.5 \leq D2/D1 \leq 6$ is satisfied, where D1 is a value of a diffusion resistance of the measurement gas flowing from an outside edge position of the first gas inlet to the sensing electrode via the main gas distribution part, and D2 is a value of a diffusion resistance of the measurement gas flowing from an outside edge position of the second gas inlet to the sensing electrode.

According to the present invention, when an exhaust gas from an engine mounted in a diesel car is a measurement gas, which has, for example, an oxygen concentration of about 1 vol % to 20 vol %, the concentration of an unburned hydrocarbon gas being a predetermined gas component present in the measurement gas can be determined accurately without being subjected to the influence of the oxygen concentration.

The present invention therefore has an object to provide a gas sensor having excellent detection sensitivity and excellent responsiveness to a detection target gas component present in a measurement gas.

BRIEF DESCRIPTION OF THE DRAWINGS

FIG. 4 illustrates, for varied external $O_2$ concentration and varied HC concentration, the relationship between an HC concentration and a value of Emf at the sensing electrode;

FIG. 5 is a configuration view of a gas sensor 100B including a sensor element 101B including an oxygen monitor electrode 42 located at a position different from that of FIGS. 1A and 1B;

FIGS. 6A and 6B are schematic views of an example configuration of a gas sensor 150 according to a second embodiment;

FIGS. 8A and 8B are schematic views of an example configuration of a gas sensor 250 according to a fourth embodiment;

DESCRIPTION OF THE PREFERRED EMBODIMENTS

First Embodiment

Outline Configuration of Gas Sensor

Figures 1A, 1B:
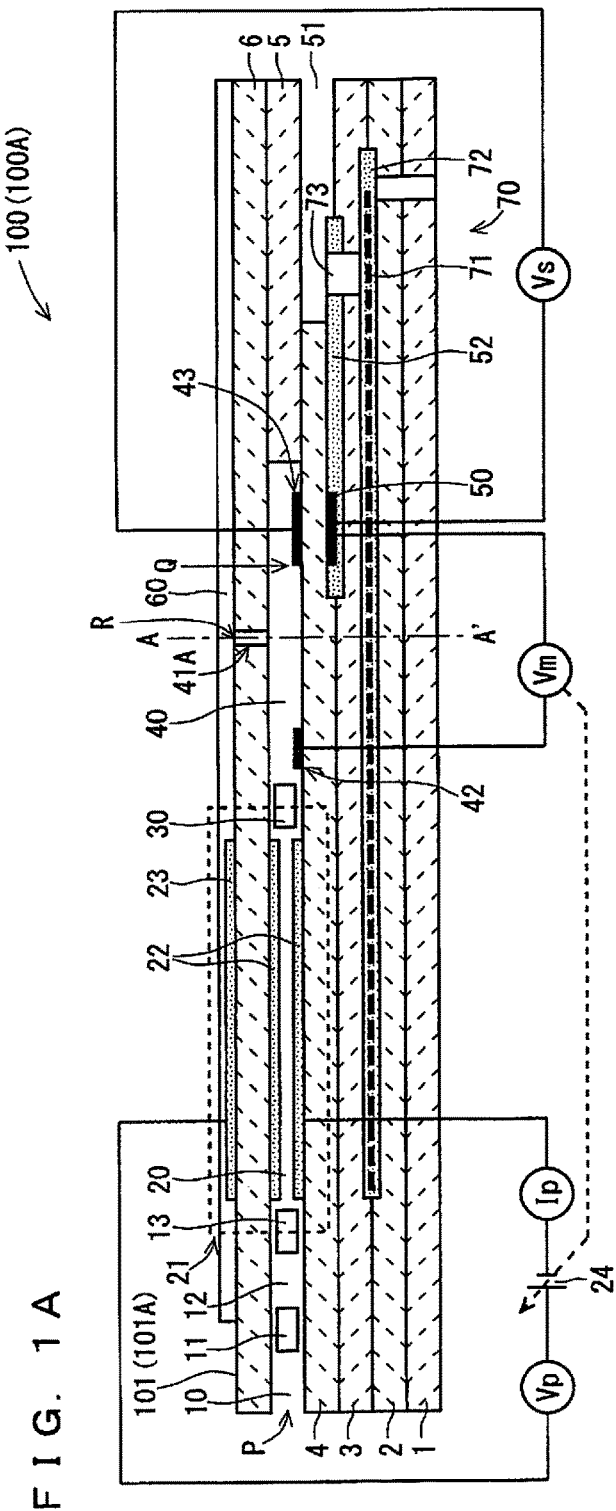
FIGS. 1A and 1B are schematic views showing an example configuration of a gas sensor 100 (100A) according to a first embodiment.

FIGS. 1A and 1B are schematic cross-sectional views of an example configuration of a gas sensor 100 (100A) according to a first embodiment of the present invention. FIG. 1A is a configuration view of the gas sensor 100A, which includes a vertical cross-section of a sensor element (101) 101A being a main component of the gas sensor 100 (100A), which is taken along the longitudinal direction (hereinafter, referred to as an element longitudinal direction) of the sensor element 100 (101A). FIG. 1B is a schematic cross-sectional view showing a cross-section of the sensor element 101A vertical to the element longitudinal direction taken along a position A-A' of FIG. 1A.

The gas sensor 100 according to this embodiment is a so-called mixed-potential gas sensor. Generally speaking, the gas sensor 100 determines the concentration of the gas component of a measurement gas, using a potential difference that occurs on the basis of the principle of mixed potential between a sensing electrode 43 and a reference electrode 50, which are provided inside the sensor element 101 mainly composed of ceramic being an oxygen-ion conductive solid electrolyte such as zirconia ($ZrO_2$), due to a difference in the concentration of a gas component being a measurement target between the portions near the electrodes.

In particular, the gas sensor 100 according to this embodiment preferably determines the concentration of an unburned hydrocarbon gas of a measurement gas, where the measurement gas is an exhaust gas present in an exhaust pipe of an engine mounted in a diesel car. In the specification, examples of the unburned hydrocarbon gas include carbon monoxide (CO) and hydrogen in addition to typical hydrocarbon gases (gases classified as hydrocarbon in terms of chemical formula) such as $C_2H_4$, $C_3H_6$, and n-C8. In the presence of a plurality of unburned hydrocarbon gases in a measurement gas, a potential difference occurring between the sensing electrode 43 and the reference electrode 50 has a value reflecting all the plurality of unburned hydrocarbon gases, and thus, a concentration value to be determined is also a total sum of the concentrations of the plurality of unburned hydrocarbon gases.

The sensor element 101 has the structure in which six layers, namely, a first substrate layer 1, a second substrate layer 2, a third substrate layer 3, a first solid electrolyte layer 4, a spacer layer 5, and a second solid electrolyte layer 6, each formed of an oxygen-ion conductive solid electrolyte, are laminated in the stated order from the bottom side of FIGS. 1A and 1B. The sensor element 101 additionally includes other components, such as the sensing electrode 43 and the reference electrode 50, mainly between those layers or on an outer peripheral surface of the element. The solid electrolytes constituting those six layers are fully airtight. Such a sensor element 101 is manufactured by, for example, laminating ceramic green sheets corresponding to the individual layers, which have been subjected to a predetermined process and printing of a circuit pattern, and further, by integrating the laminated layers through firing.

As shown in FIG. 1A, the sensor element 101 may include a surface protective layer 60 on an upper surface of the second solid electrolyte layer 6 being one surface of the sensor element 101 (FIG. 1B does not show the surface protective layer 60). The surface protective layer 60 is a porous layer made of alumina, which is provided on the upper surface of the second solid electrolyte layer 6. The surface protective layer 60 is provided to adsorb or capture airborne particles, metallic elements, or the like in a measurement gas that adversely affects sensing of an unburned hydrocarbon gas by the gas sensor 100. The surface protective layer 60 is formed to have such porosity and pore size as not to control the diffusion of the measurement gas.

Provided between a lower surface of the second solid electrolyte layer 6 and an upper surface of the first solid electrolyte layer 4 on one-end-portion side of the sensor element 101 are a first gas inlet 10, a first diffusion control part 11, a first internal space 20, a second diffusion control part 30, and a second internal space 40. That is, the sensor element 101 is a so-called in-line two-chamber sensor element. A buffer space 12 and a third diffusion control part 13 may be further provided between the first diffusion control part 11 and the first internal space 20. The first gas inlet 10, the first diffusion control part 11, the buffer space 12, the third diffusion control part 13, the first internal space 20, the second diffusion control part 30, and the second internal space 40 are adjacently formed so as to communicate with one another in the stated order. The part extending from the first gas inlet 10 to the second internal space 40 is referred to as a main gas distribution part as well.

The first gas inlet 10, the buffer space 12, the first internal space 20, and the second internal space 40 are interior spaces provided by hollowing out the spacer layer 5. The buffer space 12, the first internal space 20, and the second internal space 40 are each provided, with its upper portion defined by the lower surface of the second solid electrolyte layer 6, its lower portion defined by the upper surface of the first solid electrolyte layer 4, and its side portion defined by a side surface of the spacer layer 5.

The first diffusion control part 11, the second diffusion control part 30, and the third diffusion control part 13 are each provided as two horizontally long slits (which are openings longitudinally extending to be vertical to the sheet of FIG. 1A).

At a position that is between an upper surface of the third substrate layer 3 and a lower surface of the spacer layer 5 and is farther from the distal-end side than the gas distribution part, a reference gas introduction space 51 is provided. The reference gas introduction space 51 is an interior space with its upper portion defined by the lower surface of the spacer layer 5, its lower portion defined by the upper surface of the third substrate layer 3, and its side portion defined by a side surface of the first solid electrolyte layer 4. The air is introduced into the reference gas introduction space 51 as a reference gas.

The first gas inlet 10 is a part being open to the outside. Through this first gas inlet 10, a measurement gas is taken into the sensor element 101 from the outside.

The first diffusion control part 11 is a part that applies a predetermined diffusion resistance to the measurement gas taken through the first gas inlet 10.

The buffer space 12 is provided to cancel concentration fluctuations of the measurement gas which are caused due to pressure fluctuations of the measurement gas in the outside (in a case where the measurement gas is an automobile exhaust gas, pulsations of the exhaust gas pressure). The sensor element 101 does not necessarily need to include the buffer space 12.

The third diffusion control part 13 is a part that applies a predetermined diffusion resistance to the measurement gas introduced from the buffer space 12 into the first internal space 20. The third diffusion control part 13 is a part provided in association with the provision of the buffer space 12.

The first diffusion control part 11 and the first internal space 20 directly communicate with each other if the buffer space 12 and the third diffusion control part 13 are not provided.

The first internal space 20 is provided as a space for adjusting an oxygen partial pressure of the measurement gas introduced through the first gas inlet 10. This oxygen partial pressure is adjusted through the operation of an oxygen pumping cell 21.

The oxygen pumping cell 21 is an electrochemical pumping cell formed of an inside pump electrode 22, an outside pump electrode 23, and the oxygen-ion conductive solid electrolyte sandwiched between these electrodes. The inside pump electrode 22 is provided on substantially the entire upper surface of the first solid electrolyte layer 4, substantially the entire lower surface of the second solid electrolyte layer 6, and substantially the entire side surface of the spacer layer 5, those surfaces defining the first internal space 20. The outside pump electrode 23 is provided in the region corresponding to the inside pump electrode 22 on the upper surface of the second solid electrolyte layer 6. The inside pump electrode 22 and the outside pump electrode 23 are each formed as a porous cermet electrode rectangular in plan view (for example, a cermet electrode made of a precious metal such as Pt containing 0.1 wt % to 30.0 wt % of Au, and $ZrO_2$). In the case where the surface protective layer 60 is provided as shown in FIG. 1A, the outside pump electrode 23 is protected by the surface protective layer 60.

The oxygen pumping cell 21 causes, upon application of a pump voltage Vp by a variable power source 24 provided outside the sensor element 101, a pump current Ip to flow between the outside pump electrode 23 and the inside pump electrode 22, allowing oxygen in the first internal space 20 to be pumped out to the outside or outside oxygen to be pumped into the first internal space 20.

The second diffusion control part 30 is a part that applies a predetermined diffusion resistance to the measurement gas introduced from the first internal space 20 into the second internal space 40.

The second internal space 40 is provided as a space for performing the process for measuring the concentration of the unburned hydrocarbon gas in the measurement gas introduced through the second diffusion control part 30.

The second internal space 40 is provided with a second gas inlet 41A penetrating the second solid electrolyte layer 6 to be in communication therewith, and is also provided with an oxygen monitor electrode 42 and the sensing electrode 43.

The second gas inlet 41A is a columnar through-hole provided separately from the main gas distribution part continuous from the first gas inlet 10, to introduce a measurement gas from the outside directly to the second internal space 40 under a predetermined diffusion resistance. The second gas inlet 41A is provided to cause the outside and the second internal space 40 to directly connect with each other. The second gas inlet 41A is preferably provided along the thickness direction (the lamination direction of the layers) of the sensor element 101 in almost the center of the second internal space 40 in the element longitudinal direction and also in almost the center thereof in the element width direction (the horizontal direction of the sheet of FIG. 1B). The cross-sectional shape of the second gas inlet 41A may be oval, for example, circular, or may be polygonal, for example, rectangular.

As described above, the gas sensor 100 may be provided with the surface protective layer 60 on the upper surface of the second solid electrolyte layer 6. However, the surface protective layer 60 substantially applies no diffusion resistance to the measurement gas, and thus, the second gas inlet 41A can be regarded as causing the outside and the second internal space 40 to directly communicate with each other. Thus, the measurement gas introduced through the second gas inlet 41A is substantially controlled only to a diffusion resistance applied by the second gas inlet 41A.

The oxygen monitor electrode 42 is an electrode provided for monitoring an oxygen concentration (oxygen partial pressure) in the second internal space 40. The oxygen monitor electrode 42 is formed of a porous cermet made of Pt and zirconia as an electrode rectangular in plan view.

While the oxygen monitor electrode 42 is disposed in the second internal space 40 near the second diffusion control part 30 on the lower surface of the second internal space 40 (the upper surface of the first solid electrolyte layer 4) with reference to FIG. 1A, the oxygen monitor electrode 42 may be disposed differently.

The sensing electrode 43 is an electrode for sensing a measurement gas. The sensing electrode 43 is formed as a porous cermet electrode made of Pt containing a predetermined ratio of Au, namely, Pt—Au alloy and zirconia. Such a sensing electrode 43 is provided in the second internal space 40 at a position farther from the second diffusion control part 30 than the second gas inlet 41A.

The catalytic activation of the sensing electrode 43 against an unburned hydrocarbon gas is disabled by preferably determining the composition of a Pt—Au alloy being its constituent material. That is, the decomposition reaction of an unburned hydrocarbon gas in the sensing electrode 43 is suppressed. In the gas sensor 100, accordingly, the potential of the sensing electrode 43 selectively varies with respect to (has correlation with) the unburned hydrocarbon gas in accordance with the concentration of the unburned hydrocarbon gas. In other words, the sensing electrode 43 is provided so as to have high dependence of potential on concentration for an unburned hydrocarbon gas while having low dependence of potential on concentration for components of other measurement gas.

Below the sensing electrode 43, the reference electrode 50 is provided between the third substrate layer 3 and the first solid electrolyte layer 4. The reference electrode 50 is an electrode formed of a porous cermet similar to that of the outside pumping electrode 23 or the like, which is substantially rectangular in plan view. Provided around the reference electrode 50 is a reference gas introduction layer 52 that is made of porous alumina and communicates with the reference gas introduction space 51, and a reference gas in the reference gas introduction space 51 is introduced into the surface of the reference electrode 50.

The reference electrode 50 is used as a potential reference in the oxygen monitor electrode 42 and the sensing electrode 43. Specifically, a potential difference Vm between the oxygen monitor electrode 42 and the reference electrode 50 is used to control the oxygen concentration (oxygen partial pressure) of the measurement gas in the second internal space 40 to a predetermined value. The potential difference Vm occurs in accordance with a difference between the oxygen concentration in the atmosphere of the second internal space 40 (more strictly, the atmosphere around the oxygen monitor electrode 42) and the oxygen concentration of the reference gas. A potential difference Vs (also referred to as Emf at the sensing electrode) between the sensing electrode 43 and the reference electrode 50 is used to calculate the concentration of an unburned hydrocarbon gas in the measurement gas. The potential difference Vs occurs in accordance with a difference between the concentration of an unburned hydrocarbon gas in the atmosphere of the second internal space 40 (more strictly, the atmosphere around the sensing electrode 43) and the concentration of an unburned hydrocarbon gas in the reference gas.

The sensor element 101 further includes a heater part 70. The heater part 70 mainly includes a heater 71, a heater insulating layer 72, and a pressure diffusion hole 73.

The heater 71 is formed while being vertically sandwiched between the second substrate layer 2 and the third substrate layer 3. The heater 71 generates heat by being fed power from the outside via a heater electrode (not shown) provided on the lower surface of the first substrate layer 1. The heat generation by the heater 71 enhances the oxygen ion conductivity of the solid electrolytes constituting the sensor element 101. The heater 71 is buried over at least the entire range from the first internal space 20 to the second internal space 40 and, with reference to FIG. 1A, is provided in a range up to the reference introduction gas space 51. The provision of the heater 71 allows the gas sensor 100 to heat a predetermined place of the sensor element 101 to a predetermined temperature and maintain the predetermined temperature. The heater 71 is provided so as to meander in the longitudinal direction of the sensor element 101.

The heater insulating layer 72 is a layer formed on the upper and lower surfaces of the heater 71 for the electrical insulation between the second substrate layer 2 and the heater 71 and for the electrical insulation between the third substrate layer 3 and the heater 71. The heater insulating layer 72 is made of, for example, alumina.

The pressure diffusion hole 73 is a part formed to penetrate the substrate layer 3 and to cause the reference gas introduction space 51 and the reference gas introduction space 51 to communicate with each other. The pressure diffusion hole 73 is provided to mitigate an internal pressure rise associated with a temperature rise in the heater insulating layer 72.

<Identifying Concentration of Unburned Hydrocarbon Gas>

To sense an unburned hydrocarbon gas of a measurement gas and determine its concentration using the gas sensor 100 (100A) having the above-mentioned configuration, the sensor element 101 (101A) is placed under the atmosphere of a measurement gas containing oxygen, water vapor ($H_2O$), and inert gas such as nitrogen, and other gas in addition to an unburned hydrocarbon gas. So, the measurement gas is introduced into the sensor element 101 (101A) through the first gas inlet 10 and the second gas inlet 41A.

The measurement gas introduced into the sensor element 101 (101A) through the first gas inlet 10, which has been applied with a predetermined diffusion resistance by the first diffusion control part 11 or further by the third diffusion control part 13, reaches the first internal space 20.

In the first internal space 20, the operation of the oxygen pumping cell 21 causes oxygen to be pumped in from the outside or pumped out to the outside, so that the oxygen concentration (oxygen partial pressure) of the measurement gas present in the first internal space 20, that is, the oxygen concentration of the measurement gas flowing into the second internal space 40 through the second diffusion control part 30 is adjusted. In this embodiment, this adjustment of oxygen concentration (oxygen partial pressure) is performed so as to maintain an oxygen concentration (oxygen partial pressure) in the second internal space 40 at a predetermined value (oxygen-concentration target value) of 1 vol % or more (so as to maintain an oxygen partial pressure at a predetermined value (oxygen-partial-pressure target value) of $1 \times 10^{-2}$ atm or more). The oxygen-concentration target value is, for example, 10 vol %.

Here, the reason why the oxygen concentration in the second internal space 40 is set to 1 vol % or more (the oxygen partial pressure is set to $1 \times 10^{-2}$ atm or more) is to reduce the dependence of the mixed potential on the oxygen concentration, which is generated in accordance with the concentration of an unburned hydrocarbon gas in the sensing electrode 43, to such an extent that does not affect the calculation of the concentration of an unburned hydrocarbon gas.

An oxygen concentration of 1 vol % or more is higher than the oxygen concentration in a so-called stoichiometric composition, which corresponds to, for example, an oxygen concentration range (about 1 vol % to 20 vol %) of an exhaust gas generated when an engine mounted in a diesel car is in lean operation.

Actual pumping-in or pumping-out of oxygen is implemented by preliminarily determining a target value of the potential difference Vm between the oxygen monitor electrode 42 provided in the second internal space 40 and the reference electrode 50 to a predetermined value corresponding to an oxygen concentration (oxygen partial pressure) desired to be obtained in the second internal space 40 and then causing the variable power source 24 to control the pumping voltage Vp to be applied to the oxygen pumping cell 21 or the pump current Ip flowing through the oxygen pumping cell 21 in accordance with an actual value of the potential difference Vm and a target value.

The measurement gas flows into the second internal space 40 also from the second gas inlet 41A, and thus, the adjustment of the oxygen concentration (oxygen partial pressure) in the second internal space 40 is performed with including the oxygen in the measurement gas flowing through the second gas inlet 41A in its target. As described below, however, the sensor element 101 is configured such that as to the gases flowing into the second internal space 40, the gas flowing from the main gas distribution part via the first internal space 20 through the first gas inlet 10 prevails over the gas flowing directly through the second gas inlet 41A. Thus, the oxygen pumping cell 21 substantially pumps oxygen in or out such that the oxygen concentration (oxygen partial pressure) in the first internal space 20 reaches an oxygen-concentration target value (oxygen-partial-pressure target value).

As described above, the oxygen concentration in the first internal space 20 is set to a value close to the oxygen concentration target value higher than the value of the stoichiometric composition, and thus, an unburned hydrocarbon gas present in the first internal space 20 disappears by reacting with (by burning) the oxygen present in the first internal space 20. Accordingly, flowing into the second internal space 40 from the first internal space 20 via the second diffusion control part 30 is a gas (hereinafter, referred to as a burned gas) that has an oxygen concentration (oxygen partial pressure) adjusted to a predetermined value and contains no unburned hydrocarbon gas. Thus, present in the second internal space 40 are oxygen having a constant concentration and a gas component other than the oxygen contained in a measurement gas directly flowing from the second gas inlet 41A. This means that the gas sensor 100 is constituted to determine the concentration of an unburned hydrocarbon contained in a measurement gas flowing from the second gas inlet 41A under the condition of a constant oxygen concentration.

In the second internal space 40 into which a measurement gas and a burned gas flow in the above-mentioned manner, a mixed potential corresponding to a surrounding atmospheric gas occurs in the sensing electrode 43. Between the sensing electrode 43 and the reference electrode 50 placed under the reference gas atmosphere, a potential difference Vs corresponding to a difference in atmosphere between the electrodes occurs. As described above, however, the potential of the reference electrode 50 placed under the atmosphere of a reference gas (air) having a constant oxygen concentration is maintained constant. Further, the dependence of mixed potential on oxygen concentration is reduced in the sensing electrode 43, and the potential of the sensing electrode 43 selectively has dependence on concentration for an unburned hydrocarbon gas in a measurement gas. Thus, the potential difference Vs between the sensing electrode 43 and the reference electrode 50 practically has a value corresponding to the composition of the measurement gas surrounding the sensing electrode 43. Therefore, a certain functional relation (referred to as sensitivity characteristics) holds between the concentration of an unburned hydrocarbon gas and the potential difference Vs.

Sensitivity characteristics are experimentally identified in advance by measuring a potential difference Vs, where a plurality of different mixed gases, each of which has a known concentration of an unburned hydrocarbon gas, are used as measurement gases. In actual use of the gas sensor 100, accordingly, the concentration of an unburned hydrocarbon gas in a measurement gas can be determined almost in real time by converting the potential difference Vs that varies from moment to moment in accordance with the concentration of the unburned hydrocarbon gas of the measurement gas into the concentration of the unburned hydrocarbon gas on the basis of the sensitivity characteristics in a calculation processing unit (not shown).

To actually calculate the concentration of an unburned hydrocarbon gas with accuracy, however, the flow rate of a measurement gas, flowing directly into the second internal space 40 through the second gas inlet 41A to reach the area near the sensing electrode 43, and the flow rate of a burned gas, having a concentration of oxygen flowing from the main gas distribution part that is almost close to the oxygen-concentration target value, need to be balanced preferably. Such balance can be evaluated on the basis of the magnitude of a ratio D2/D1 of a diffusion resistance (D2) applied to a measurement gas flowing through the second gas inlet 41A until the gas reaches the sensing electrode 43 to a diffusion resistance (D1) applied to a burned gas until the gas reaches the sensing electrode 43 from the first gas inlet 10. In more detail, the diffusion resistance D1 is a diffusion resistance between the edge position P of the first gas inlet 10 and the position Q of the sensing electrode 43 in FIG. 1A, and the diffusion resistance D2 is a diffusion resistance between an edge position R of the second gas inlet 41A and the position Q of the sensing electrode 43.

An excessively small value of the ratio D2/D1 results in an excessively large inflow of the measurement gas from the second gas inlet 41A with respect to the inflow of the burned gas, leading to easily varying oxygen concentration in the second internal space 40. This makes it difficult to control the oxygen concentration to have an oxygen concentration target value. Meanwhile, an excessively large value of the ratio D2/D1 results in an excessively small inflow of the measurement gas with respect to the inflow of the burned gas, reducing an absolute amount of the unburned hydrocarbon gas to be introduced into the second internal space 40. Consequently, sufficient sensitivity cannot be obtained (the value of the potential difference Vs is excessively small). In any case, the accuracy of calculating an unburned hydrocarbon concentration unfavorably reduces.

In this embodiment, the sensor element 101 configured so as to satisfy 3.5≤D2/D1≤6 enables a gas sensor 100 having excellent oxygen concentration controllability and excellent detection sensitivity to an unburned hydrocarbon gas.

Table 1 shows the evaluation results of the oxygen concentration ($O_2$ concentration) controllability and the output sensitivity to an unburned hydrocarbon gas (HC output sensitivity) for seven gas sensors 100 produced by varying the value of the diffusion resistance ratio D2/D1. Specifically, Table 1 shows the evaluation results when measurement gases containing 1000 ppm of $C_2H_4$ as unburned hydrocarbon and having oxygen concentrations (external $O_2$ concentrations) varying in the range of 1 vol % to 20 vol % are prepared, and the respective gas sensors 100 are operated.

TABLE 1

| Diffusion Resistance Ratio D2/D1 | $O_2$ Concentration Controllability | HC Output Sensitivity |
|---|---|---|
| 1.2 | X | ◯ |
| 2.0 | Δ | ◯ |
| 3.5 | ◯ | ◯ |
| 5.3 | ◯ | ◯ |
| 6.0 | ◯ | ◯ |
| 7.9 | ◯ | Δ |
| 10.5 | ◯ | X |

With reference to Table 1, in the case that an actual oxygen concentration falls within a range of values±10% of the oxygen concentration (target value) desired to be achieved in the second internal space 40, the oxygen concentration controllability is judged excellent and a mark "◯" (circle) is placed in the column "$O_2$ concentration controllability." In the case that an actual oxygen concentration falls within a range of values±20% of the target value though it does not meet the requirements for the mark "◯," a mark "Δ" (triangle) is placed in the column "$O_2$ concentration controllability." In the case that an actual oxygen concentration does not correspond to either case, a mark "X" (christcross) is placed in the column "$O_2$ concentration controllability."

As to output sensitivity, 150 mV is set as a target value (sensitivity target value) of Emf at the sensing electrode, and in the case that Emf at the sensing electrode is equal to or higher than the sensitivity target value, the output sensitivity to an unburned hydrocarbon gas is judged excellent and a mark "◯" (circle) is placed in the column "HC output sensitivity." In the case that the sensitivity target value is 50 mV or more and 150 mV or less, a mark "Δ" (triangle) is placed in the column "HC output sensitivity." In the case that the sensitivity target value is less than 50 mV, a mark "X" (christcross) is placed in the column "HC output sensitivity."

Figure 2:
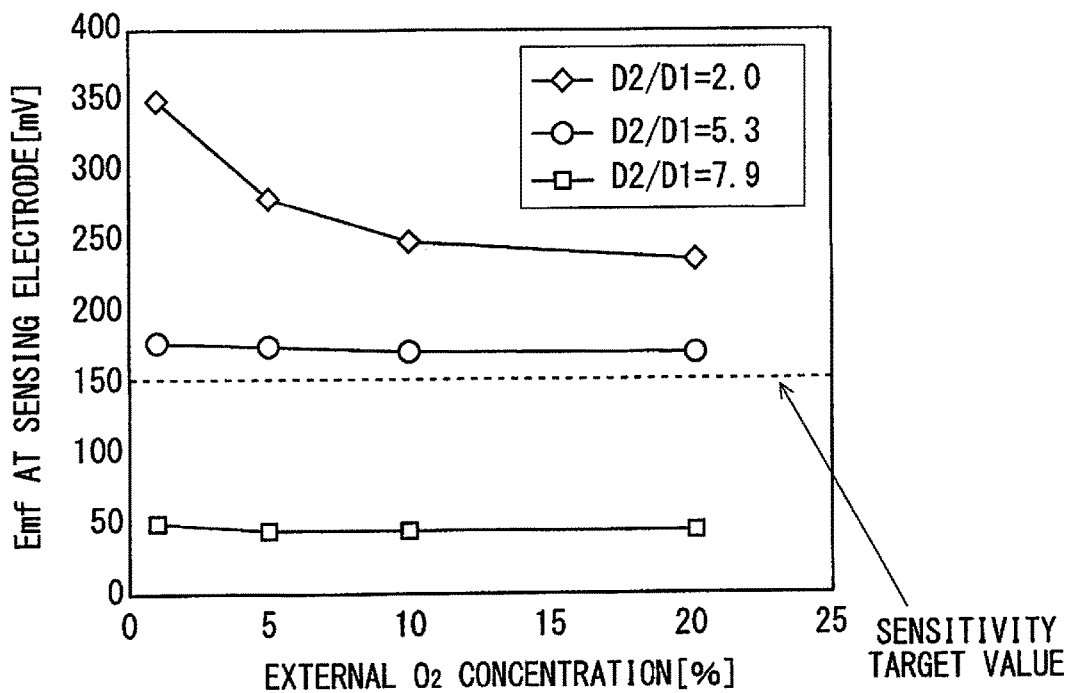
FIG. 2 shows the dependence of a value of Emf at the sensing electrode, which is a potential difference between a sensing electrode 43 and a reference electrode 50, on an external $O_2$ concentration.

FIG. 2 shows the dependence of the value of Emf of the sensing electrode, being a potential difference between the sensing electrode 43 and the reference electrode 50, on the external $O_2$ concentration for three of the seven gas sensors 100.

FIG. 2 illustrates the cases where the value of the diffusion resistance ratio D2/D1 is 2.0, 5.3, and 7.9.

The results of Table 1 and FIG. 2 confirm that a gas sensor 100 having excellent oxygen concentration controllability and excellent detection sensitivity to an unburned hydrocarbon gas can be achieved by satisfying 3.5≤D2/D1≤6.

Figure 3:
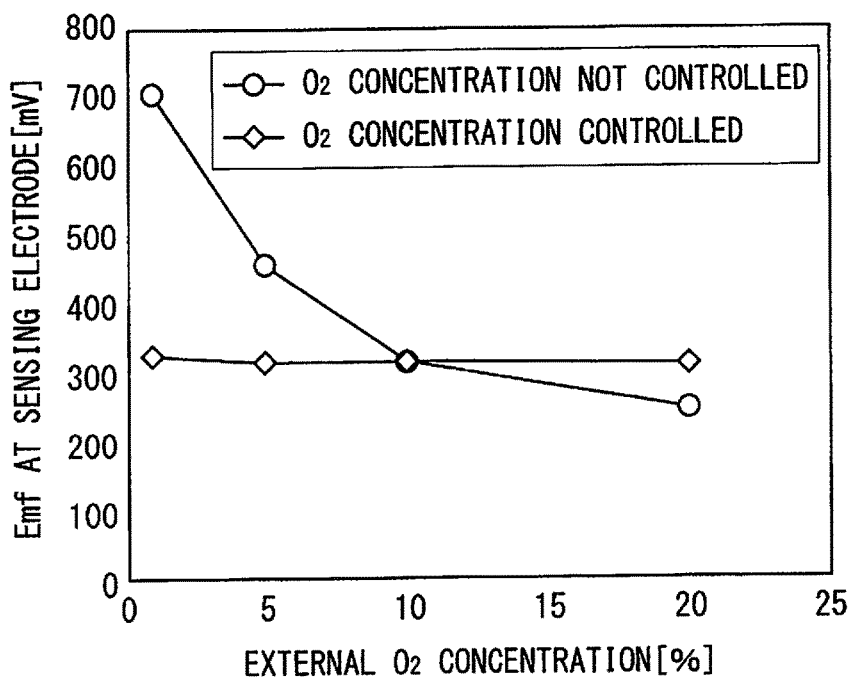
FIG. 3 illustrates the effects of controlling an oxygen concentration in a second internal space 40.

FIG. 3 illustrates the effects of controlling oxygen concentration in the second internal space 40. Specifically, FIG. 3 shows the dependence of the value of Emf at the sensing electrode on the external $O_2$ concentration in the cases where the oxygen concentration in the second internal space 40 is controlled and is not controlled on the same measurement gas conditions as those of the case shown in FIG. 2 for one gas sensor 100 having a diffusion resistance ratio D2/D1 of 5.3.

The results shown in FIG. 3 confirm that the gas sensor 100 can obtain a stable Emf at the sensing electrode independent of an external $O_2$ concentration by controlling the oxygen concentration in the second internal space 40 to be constant.

FIG. 4 illustrates the relationship between the concentration of an unburned hydrocarbon gas (HC concentration) and the value of Emf at the sensing electrode for varying external $O_2$ concentrations and varying HC concentrations of the same gas sensor 100 as that of FIG. 3. With reference to FIG. 4, the correspondence between the HC concentration and Emf of the sensing electrode is substantially the same independent of external $O_2$ concentration. This means that the sensitivity characteristics of the gas sensor 100 are maintained at substantially the same level for different external $O_2$ concentrations. The results of FIG. 4 confirm that the gas sensor 100 according to this embodiment can accurately determine the concentration of an unburned hydrocarbon gas for different external $O_2$ concentrations.

Although the value of the diffusion resistance D1 corresponds to the structure of the main gas distribution part (such as the structure of each diffusion control part and whether the third diffusion control part 13 is provided), the value of the diffusion resistance D2 is determined almost by the diffusion resistance (D2α) of the second gas inlet 41A. Such a value of the diffusion resistance D2α depends on a distance L between the edge position R and the second internal space 40 and a cross-section S of the second gas inlet 41A. Specifically, letting the diffusion coefficient (constant) be D0, the relationship D2α=D0×(L/S) holds. Here, the distance L has a value corresponding to the thickness of the second solid electrolyte layer 6, and thus, a value that the distance L can take matches a value that the second solid electrolyte layer 6 can take. Specifically, the distance L can take values of about 50 μm to 350 μm. The value that the cross-section S can take is about $2.0\times10^{-7}$ cm or more. The minimum value corresponds to a value when the second gas inlet 41A is formed so as to have a circular cross-section with a radius of about 5 μm.

As described above, in this embodiment, a second gas inlet that causes the second internal space and the outside to directly communicate with each other is provided, separately from the main gas distribution part extending from the first gas inlet to the second internal space, to an in-line two-chamber sensor element including two internal spaces communicating with each other in the element longitudinal direction in the gas sensor. Besides, an oxygen monitor electrode and a sensing electrode that selectively senses an unburned hydrocarbon gas are provided in the second internal space. In that case, the rate D2/D1 of the diffusion resistance D2, applied to a measurement gas flowing through the second gas inlet until the gas reaches the sensing electrode, to the diffusion resistance D1, applied to a burned gas until the gas reaches the sensing electrode from the first gas inlet, satisfies 3.5≤D2/D1≤6. Through pumping-in of oxygen by the oxygen pumping cell provided in the first internal space, the oxygen concentration of the second internal space is controlled to a predetermined value of 1 vol % or more on the basis of the potential difference between the oxygen monitor electrode and the reference electrode. In this state, on the basis of the potential difference between the sensing electrode and the reference electrode occurring in accordance with the concentration of the unburned hydrocarbon gas of the measurement gas introduced from the second gas inlet, and the relationship between this potential difference and the concentration of an unburned hydrocarbon gas identified in advance, the concentration of an unburned hydrocarbon gas of a measurement gas is determined. As a result, the concentration of an unburned hydrocarbon gas present in an exhaust gas from the engine mounted in a diesel car, whose oxygen concentration is about 1 vol % to 20 vol %, can be determined accurately without being subjected to the influence of the oxygen concentration.

<Modification of Position of Oxygen Monitor Electrode>

Although the oxygen monitor electrode 42 is provided at a position (upstream position) that is closer to the second diffusion control part 30 than a position of the second gas inlet 41A and that is on the lower surface (the upper surface of the first solid electrolyte layer 4) of the second internal space 40 with reference to FIG. 1A, the oxygen monitor electrode 42 may be provided in other position. For example, the oxygen monitor electrode 42 may be provided on the upper surface of the second internal space 40 (the lower surface of the second solid electrolyte layer 6) while its position in the element longitudinal direction is the same as that of the case shown in FIG. 1A.

FIG. 5 is a configuration view of a gas sensor 100 (100B) including a sensor element 101 (101B) including the oxygen monitor electrode 42 disposed in another different position. The sensor element 101B shown in FIG. 5 is provided with the oxygen monitor electrode 42 at a position (downstream position) farther from the second diffusion control part 30 than a position of the sensing electrode 43 and on the lower surface of the second internal space 40 (the upper surface of the first solid electrolyte layer 4). Alternatively, the oxygen monitor electrode 42 may be provided on the upper surface of the second internal space 40 (the lower surface of the second solid electrolyte layer 6) while its position in the element longitudinal direction is the same as that of the case shown in FIG. 5.

It is not preferable to provide the oxygen monitor electrode 42 between the second gas inlet 41A and the sensing electrode 43 because the unburned hydrocarbon gas of the measurement gas introduced from the second gas inlet 41A is burned in the oxygen monitor electrode 42.

Second Embodiment

FIGS. 6A and 6B are schematic views of an example configuration of a gas sensor 150 according to a second embodiment of the present invention. FIG. 6A is a configuration view of the gas sensor 150, which includes a vertical cross-section taken along the longitudinal direction (element longitudinal direction) of the sensor element 151 being a main component of the gas sensor 150. FIG. 6B is a schematic cross-sectional view of the cross-section vertical to the element longitudinal direction at a position B-B' of FIG. 6A.

The sensor element 101 of the gas sensor 100 according to the first embodiment includes the second gas inlet 41A that penetrates the second solid electrolyte layer 6 and communicates with the second internal space 40, whereas, as can be seen from FIG. 6B, the sensor element 151 of the gas sensor 150 according to the this embodiment includes a second gas inlet 41B that penetrates the spacer layer 5 in the element width direction (one of the directions perpendicular to the lamination direction of the layers) and communicates with the second internal space 40. The other components are the same as those of the gas sensor 100, which are denoted by the same references as those of the first embodiment and are not described below. Although FIG. 6A illustrates the case in which the gas sensor 150 is configured such that the oxygen monitor electrode 42 is disposed at the same position as that of the gas sensor 100A illustrated in FIG. 1A, the oxygen monitor electrode 42 may be disposed at other position as in the first embodiment.

The second gas inlet 41B is disposed in a similar manner to that of the second gas inlet 41A except for a position at which it is formed. The gas sensor 150 can also define a diffusion resistance rate D2/D1 similarly to the gas sensor 100, and can achieve excellent detection sensitivity while maintaining excellent oxygen concentration controllability by satisfying 3.5≤D2/D1≤6. For the sensor element 151, however, a value that the distance L from the edge position R to the second internal space 40 can take depends on the size of the second internal space 40 in the element width direction (the direction perpendicular to the element longitudinal direction and the element width direction). For example, when the size of the sensor element 151 in the element width direction is 4.3 mm, the size of the second internal space 40 in the direction is preferably about 1 mm to 2.3 mm, and accordingly, a value that the distance L can take is about 900 μm to 1650 μm. The cross-section S is similar to that of the first embodiment.

In other words, also in the gas sensor 150 according to this embodiment, as in the gas sensor 100 according to the first embodiment, the second gas inlet 41B is provided so as to satisfy 3.5≤D2/D1≤6, and the concentration of an unburned hydrocarbon gas of a measurement gas is determined on the basis of the sensitivity characteristics identified in advance and the potential difference between the sensing electrode and the reference electrode with the oxygen concentration of the second internal space being controlled to a predetermined value of 1 vol % or more through pumping-in of oxygen by the oxygen pumping cell 21. As a result, the concentration of an unburned hydrocarbon gas present in an exhaust gas from the engine mounted in a diesel can be determined accurately without being subjected to the influence of the oxygen concentration.

Third Embodiment

Figures 7A, 7B:
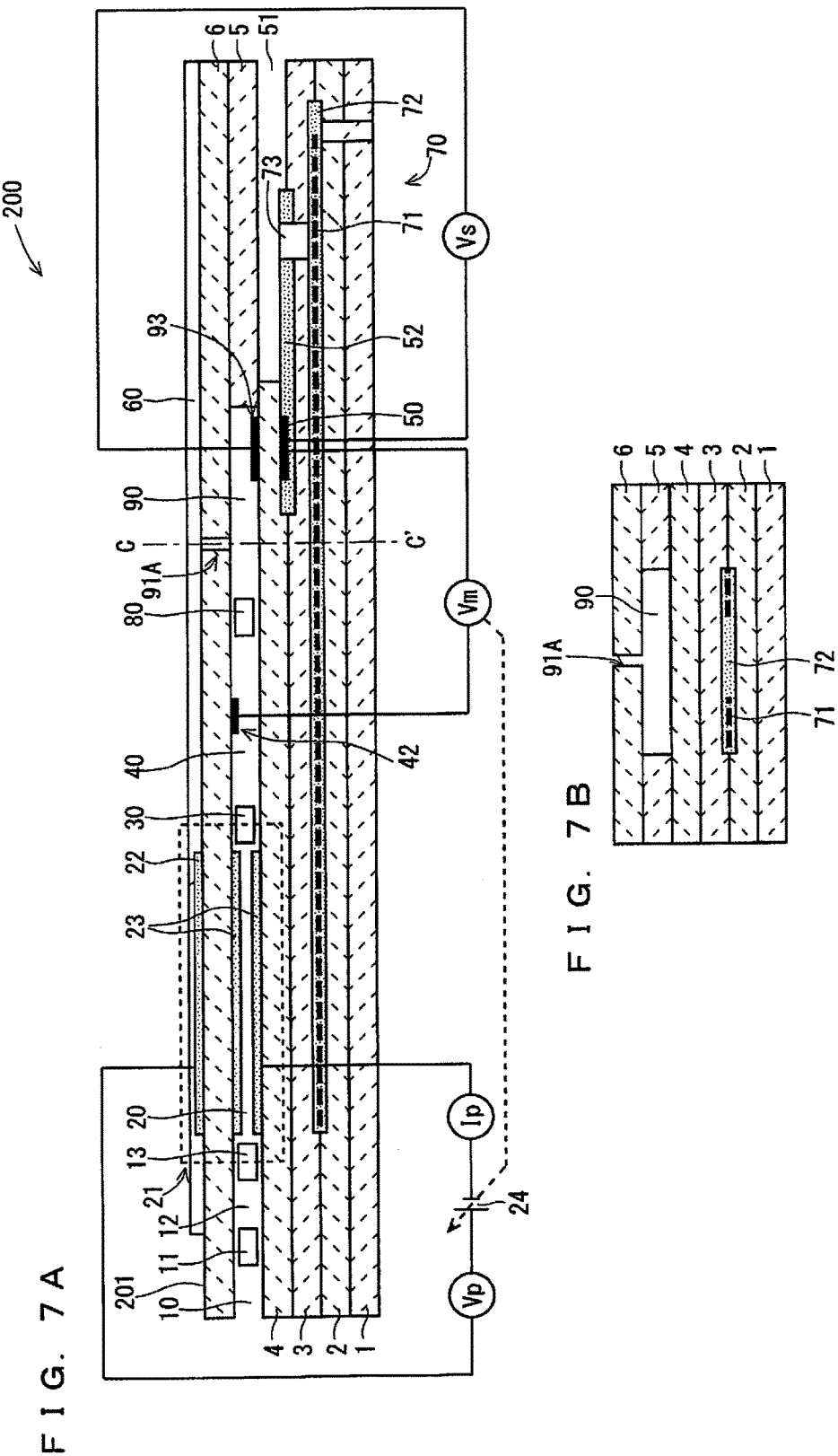
FIGS. 7A and 7B are schematic views of an example configuration of a gas sensor 200 according to a third embodiment.

FIGS. 7A and 7B are schematic views of an example configuration of a gas sensor 200 according to a third embodiment of the present invention. FIG. 7A is a configuration view of the gas sensor 200, which includes a vertical cross-section taken along the longitudinal direction (element longitudinal direction) of the sensor element 251 being a main component of the gas sensor 200. FIG. 7B is a schematic cross-sectional view of the cross-section perpendicular to the element longitudinal direction at a position C-C' of FIG. 7A.

While the sensor element 101 of the gas sensor 100 according to the first embodiment includes two internal spaces, namely, the first internal space 20 and the second internal space 40, as can be seen from FIG. 7A, the sensor element 201 of the gas sensor 200 according to this embodiment includes a third internal space 90 communicating with the second internal space 40 via a fourth diffusion control part 80, in addition to the first internal space 20 and the second internal space 40. The third internal space 90 is an internal space provided by hollowing out the spacer layer 5, similarly to the first internal space 20 and the second internal space 40. The fourth diffusion control part 80 is provided as two horizontally long slits (which are openings longitudinally extending to be vertical to the sheet of FIG. 7A), similarly to the first diffusion control part 11 or the like.

While the sensor element 101 includes the oxygen monitor electrode 42 and the sensing electrode 43 in the second internal space 40 and includes the second gas inlet 41A so as to communicate with the second internal space 40, the sensor element 201 of the gas sensor 200 according to this embodiment includes a sensing electrode 93 in the third internal space 90 and also includes a second gas inlet 91A so as to penetrate the second solid electrolyte layer 6 and cause the third internal space 90 and the outside to communicate with each other. The other components are the same as those of the gas sensor 100, which are denoted by the same references as those of the first embodiment and are not described below.

Although the oxygen monitor electrode 42 is disposed in the second internal space 40 similarly to the sensor element 101, FIG. 7A illustrates the case in which the oxygen monitor electrode 42 is disposed on the lower surface of the second solid electrolyte layer 6. As in the first and second embodiments, however, the position of the oxygen monitor electrode 42 is not limited to the above.

In this embodiment, though what is controlled on the basis of the potential difference Vm is the oxygen concentration in the second internal space 40 as in the first embodiment, it is to the third internal space 90 that the measurement gas is introduced from the second gas inlet 91A. Besides, the fourth diffusion control part 80 is provided between these internal spaces. In the sensor element 201, thus, the gas (the burned gas containing no unburned hydrocarbon gas), whose oxygen concentration has been adjusted in the second internal space 40 without being subjected to almost any influence of the measurement gas introduced from the second gas inlet 91A, is introduced into the third internal space 90 via the fourth diffusion control part 80. This allows the sensor element 201 to have stability in the oxygen concentration in the third internal space 90 being an internal space in which the sensing electrode 93 is provided.

Meanwhile, the gas sensor 200 identifies the concentration of an unburned hydrocarbon gas using a potential difference Vs between the sensing electrode 93 and the reference electrode 50, and the concentration is identified as in the first embodiment.

The gas sensor 200 can also define a diffusion resistance ratio D2/D1 similarly to the gas sensor 100, and can achieve excellent detection sensitivity while maintaining excellent oxygen concentration controllability by satisfying $3.5 \leq D2/D1 \leq 6$. Values that the distance L and the cross-section S of the second gas inlet 91A can take are similar to those of the first embodiment.

In other words, in the gas sensor 200 according to this embodiment, as in the gas sensor 100 according to the first embodiment, the second gas inlet 91A is provided so as to satisfy $3.5 \leq D2/D1 \leq 6$, and the concentration of an unburned hydrocarbon gas of a measurement gas is determined on the basis of the sensitivity characteristics identified in advance and the potential difference between the sensing electrode and the reference electrode with the oxygen concentration of the second internal space being controlled to a predetermined value of 1 vol % or more through pumping-in of oxygen by the oxygen pumping cell 21. As a result, the concentration of an unburned hydrocarbon gas present in an exhaust gas from the engine mounted in a diesel can be determined accurately without being subjected to the influence of the oxygen concentration.

Fourth Embodiment

FIGS. 8A and 8B are schematic views of an example configuration of a gas sensor 250 according to a fourth embodiment of the present invention. FIG. 8A is a configuration view of the gas sensor 250, which includes a vertical cross-section taken along the longitudinal direction (element longitudinal direction) of the sensor element 251 being a main component of the gas sensor 250. FIG. 8B is a schematic cross-sectional view of the cross-section perpendicular to the element longitudinal direction at a position D-D' of FIG. 8A.

While the sensor element 201 of the gas sensor 200 according to the third embodiment includes the second gas inlet 91A that penetrates the second solid electrolyte layer 6 and communicates with the third internal space 90, as can be seen from FIG. 8B, the sensor element 251 of the gas sensor 250 according to this embodiment includes a second gas inlet 91B that penetrates the spacer layer 5 in the element width direction and communicates with the second internal space 40. The other components are the same as those of the gas sensor 200, which are denoted by the same references as those of the third embodiment and are not described below. Although FIG. 8A illustrates the case in which the gas sensor 250 is configured such that the oxygen monitor electrode 42 is disposed at the same position as that of the gas sensor 200A illustrated in FIG. 7A, the oxygen monitor electrode 42 may be disposed at other position as in the first to third embodiments.

The second gas inlet 91B is disposed in a similar manner to that of the second gas inlet 91A except for a position at which it is formed. The gas sensor 250 can also define a diffusion resistance rate D2/D1 similarly to the gas sensor 200, and can achieve excellent detection sensitivity while maintaining excellent oxygen concentration controllability by satisfying $3.5 \leq D2/D1 \leq 6$. Values that the distance L and the cross-section S of the second gas inlet 91B can take are similar to those of the second embodiment.

In other words, also in the gas sensor 250 according to this embodiment, as in the gas sensor 200 according to the third embodiment, the second gas inlet 91B is provided so as to satisfy $3.5 \leq D2/D1 \leq 6$, a burned gas whose oxygen concentration of the second internal space is controlled to a predetermined value of 1 vol % or more is introduced into the third internal space 90, and the concentration of an unburned hydrocarbon gas of a measurement gas is determined on the basis of the potential difference between the sensing electrode and the reference electrode and the sensitivity characteristics identified in advance. As a result, the concentration of an unburned hydrocarbon gas present in an exhaust gas from the engine mounted in a diesel can be determined accurately without being subjected to the influence of the oxygen concentration.

<Process of Manufacturing Sensor Element>

The following describes the outline of the process of manufacturing the sensor elements 101, 151, 201, and 251.

In outline, any of the four sensor elements (hereinafter, also referred to as the sensor element 101 or other element) is produced by forming a laminated body formed of green sheets containing an oxygen-ion conductive solid electrolyte such as zirconia as a ceramic component and by cutting and firing the laminated body. The oxygen-ion conductive solid electrolyte may be, for example, yttrium partially stabilized zirconia (YSZ). During the production, a second gas inlet is formed at a desired position.

The process of manufacturing the sensor element 101 or other element comes in three ways depending on how to form a second gas inlet. The processes are described below in sequence.

(First Way)

Figure 9:
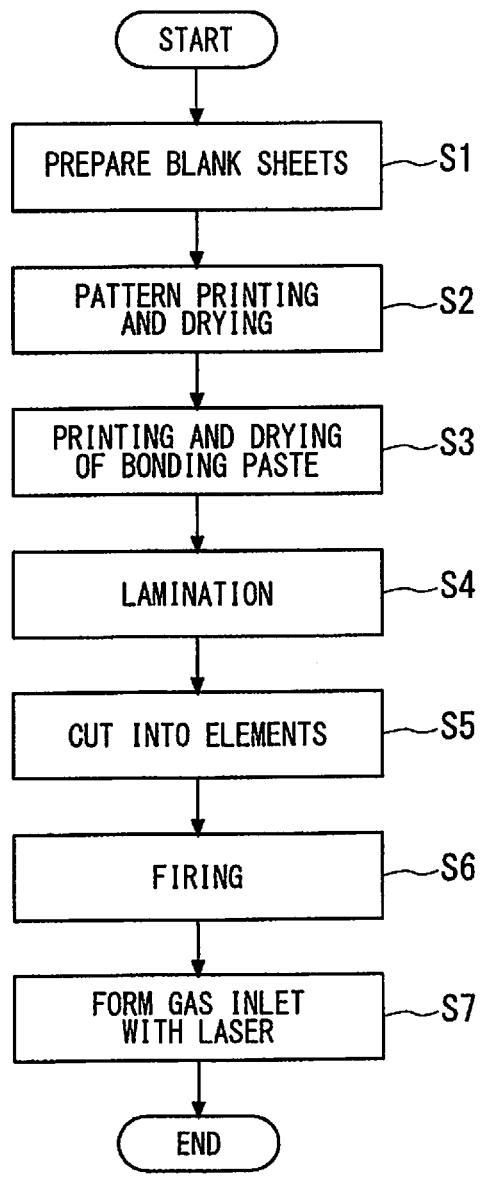
FIG. 9 shows a flow of the process of producing a sensor element 101 or other element in a first way.

FIG. 9 shows a flow of the process of producing the sensor element 101 or other element in a first way. First, blank sheets (not shown) being green sheets having no pattern formed thereon are prepared (Step S1). Specifically, six blank sheets corresponding to the first substrate layer 1, the second substrate layer 2, the third substrate layer 3, the first solid electrolyte layer 4, the spacer layer 5, and the second solid electrolyte layer 6 are prepared. A blank sheet for forming the surface protective layer 60 is prepared as well. A plurality of sheet holes for positioning in printing and lamination are provided in the blank sheets. Such sheet holes are formed in advance through, for example, punching by a punching machine. For a green sheet whose corresponding layer forms an internal space, a penetration corresponding to the internal space is provided in advance similarly through punching. All of the blank sheets corresponding to the respective layers of the sensor element 101 or other element need not to have the same thickness (the same holds true for second and third ways).

After the blank sheets corresponding to the respective layers are prepared, pattern printing and drying for forming various patterns are performed on the individual blank sheets (Step S2). Specifically, electrode patterns of, for example, the sensing electrode 43 and the reference electrode 50, the patterns for forming the reference gas introduction layer 52, internal wiring (not shown), and the like are formed through printing. In this case, patterns to form the diffusion control parts are formed at their formation positions, using a paste containing a low-temperature decomposition material that is decomposed in firing (is decomposed at a temperature of the firing) in a subsequent step (Step S6). Examples of the low-temperature decomposition material include theobromine and carbon. A cut mark is also printed on the first substrate layer 1, which is used as a reference of a cutting position for cutting a laminated body in a subsequent step.

Each pattern is printed by applying a paste for pattern formation, prepared in accordance with the characteristics required for each formation target, to the blank sheet using a known screen printing technique. Any known drying means is available for drying after printing.

After the completion of pattern printing, printing and drying of a bonding paste are performed to laminate and bond the green sheets corresponding to the respective layers (Step S3). Any known screen printing technique is available for printing of a bonding paste, and any known drying means is available for drying after printing.

Crimping is subsequently performed, in which the green sheets applied with the bonding paste are laminated in a predetermined order, and the laminated green sheets are crimped on predetermined temperature and pressure conditions, to thereby form a laminated body (Step S4). Specifically, green sheets being lamination targets are laminated while being positioned at the sheet holes to be held in a predetermined lamination jig (not shown), and the green sheets together with the lamination jig are heated and pressurized by a lamination machine such as a known hydraulic pressing machine. The pressure, temperature, and time for heating and pressurizing depend on a lamination machine to be used, whose conditions may be determined appropriately for good lamination.

After the laminated body is obtained as described above, subsequently, a plurality of parts of the laminated body are cut out into individual units (referred to as element bodies) of the sensor element 101 or other element (Step S5). The cut out element bodies are fired under predetermined conditions (Step S6). In other words, the sensor element 101 or other element is produced by integrally firing the solid electrolyte layers and the electrodes. The firing temperature is preferably 1200° C. or higher and 1500° C. or lower (for example, 1365° C.). The integral firing in such a way provides satisfactory adhesion strength to the electrodes of the sensor element 101 or other element.

Subsequently, the obtained fired body at a predetermined position is irradiated with laser light, thereby forming the second gas inlet 41A, 41B, 91A, or 91B (Step S7). Consequently, the sensor element 101 or other element is produced. A lower limit of the cross-section S is achieved when the second gas inlet 41A, 41B, 91A, or 91B is produced through laser light irradiation as in the first way.

The thus obtained sensor element 101 or other element is accommodated in a predetermined housing to be incorporated into the main body (not shown) of the gas sensor 100, 150, 200, or 250 (the same holds true for the second and third ways).

(Second Way)

Figure 10:
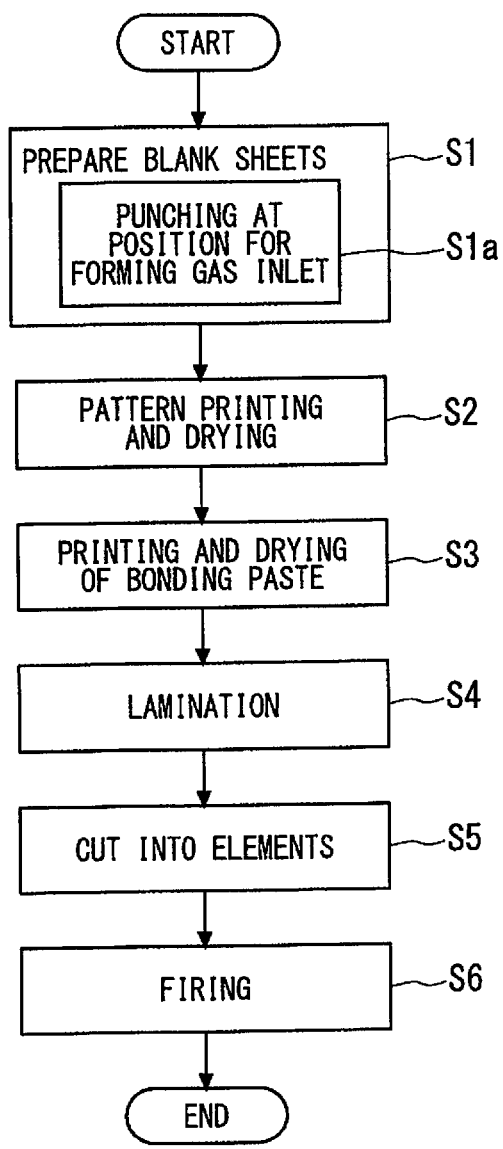
FIG. 10 shows a flow of the process of producing the sensor element 101 or other element in a second way.

FIG. 10 shows a flow of the process of producing the sensor element 101 or other element in the second way. Also in the second way, as in the first way, first, black sheets (not shown) being green sheets having no pattern formed thereon are prepared (Step S1). Specifically, six blank sheets corresponding to the first substrate layer 1, the second substrate layer 2, the third substrate layer 3, the first solid electrolyte layer 4, the spacer layer 5, and the second solid electrolyte layer 6 are prepared. A blank sheet for forming the surface protective layer 60 is prepared as well. In this case, as in the first way, sheet holes and a penetration corresponding to the internal space are provided in the black sheets. In the second way, punching is further performed at the position corresponding to the second gas inlet 41A, 41B, 91A, or 91B (Step S1a). Specifically, in the production of the sensor element 101 or the sensor element 201, a through-hole is formed at a position of the black sheet corresponding to the second solid electrolyte layer 6, at which the second gas inlet 41A or 91A is formed. Meanwhile, in the production of the sensor element 151 or the sensor element 251, a through-hole is formed at a position of the black sheet corresponding to the spacer layer 5, at which the second gas inlet 41B or 91B is formed. In this case, the thickness of the green sheet that turns into the spacer layer 5 is the punching thickness. If an excessively large cross section of the second gas inlet, which is obtained through the firing in this state, makes it difficult to obtain the required condition 3.5≤D2/D1≤6, the required condition 3.5≤D2/D1≤6 may be satisfied by appropriately filling the through-hole with a porous material prior to the firing.

Subsequently, processes similar to those of the first way are performed in Steps S2 to S6. When a fired body is obtained in Step S6, the sensor element 101 or other element including the second gas inlet 41A, 41B, 91A, or 91B provided at a desired position has been produced.

(Third Way)

Figure 11:
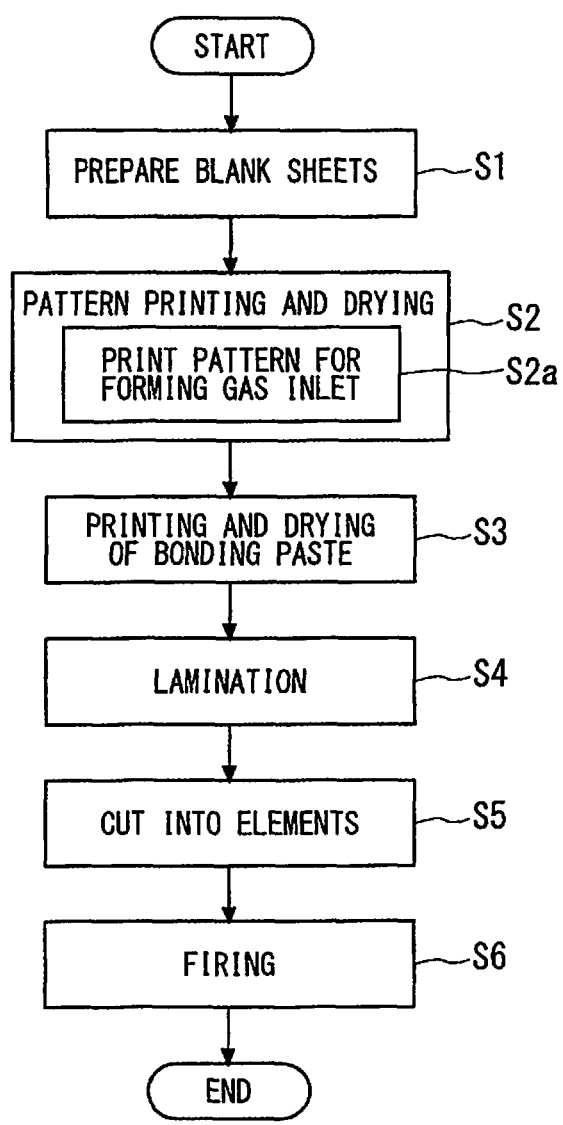
FIG. 11 shows a flow of the process of producing the sensor element 101 or other element in a third way.

FIG. 11 shows a flow of the process of producing the sensor element 101 or other element in the third way. The third way is applicable only to the production of the sensor element 151 or the sensor element 251.

First, as in the first way, six blank sheets are prepared (Step S1). Subsequently, also as in the first way, pattern printing and drying for forming various patterns are performed on the individual blank sheets (Step S2). In the third way, a paste containing a low-temperature decomposition material similar to that used in the formation of a diffusion control part is applied to a position of the green sheet that turns into the first solid electrolyte layer 4, directly on which the second gas inlet 41B or 91B is formed, in accordance with the shape of the second gas inlet 41B or 91B (Step S2a).

Subsequently, Steps S2 to S6 are performed as in the first way. When a fired body is obtained in Step S6, the sensor element 151 or 251 including the second gas inlet 41B or 91B provided at a desired position has been produced.

The invention claimed is:

1. A mixed-potential gas sensor that includes a sensor element constituted by an oxygen-ion conductive solid electrolyte and measures a concentration of a predetermined gas component of a measurement gas, said sensor element comprising:
   a first gas inlet communicating with the outside;
   a first internal space communicating with said first gas inlet via a predetermined diffusion control part;
   a second internal space communicating with said first internal space via a second predetermined diffusion control part;
   a second gas inlet causing said outside and said second internal space to directly communicate with each other;
   a sensing electrode located in said second internal space;
   a reference gas introduction space into which a reference gas is introduced;
   a reference electrode located in said reference gas introduction space;
   an oxygen pumping cell including an inside pump electrode facing said first internal space, an outside pump electrode located on an outside surface of said sensor element, and said solid electrolyte located between said inside pump electrode and said outside pump electrode; and
   a main gas distribution part being a path extending from said first gas inlet to said second internal space, wherein
   said gas sensor is configured and disposed so as to determine the concentration of said predetermined gas component contained in the measurement gas introduced from said second gas inlet into said second internal space on the basis of the potential difference between said sensing electrode and said reference electrode, while causing said oxygen pumping cell to pump oxygen in or out for said measurement gas flowing via said main gas distribution part such that an oxygen concentration of said second internal space is maintained at a constant value of 1 vol % or more, and $3.5 \leq D2/D1 \leq 6$ is satisfied, where D2/D1 is a diffusion resistance ratio, D1 is a diffusion resistance of said measurement gas flowing from an outside edge position of said first gas inlet to a position of said sensing electrode in said second internal space via said main gas distribution part, and D2 is a diffusion resistance of said measurement gas flowing from an outside edge position of said second gas inlet to said position of said sensing electrode in said second internal space.

2. The gas sensor according to claim 1, wherein
   said sensor element further comprises, in said second internal space, a monitor electrode for monitoring the oxygen concentration of said second internal space, and
   said oxygen pumping cell pumps oxygen in or out for said measurement gas flowing via said main gas distribution part on the basis of the potential difference between said monitoring electrode and said reference electrode.

3. The gas sensor according to claim 2, wherein in said second internal space, said monitoring electrode is located at an upstream position that is closer to a second diffusion control part than a position of said sensing electrode and a position of said second gas inlet.

4. The gas sensor according to claim 2, wherein in said second internal space, said monitoring electrode is located at a downstream position that is farther from the second diffusion control part than a position of said sensing electrode and a position of said second gas inlet.

5. A mixed-potential gas sensor that includes a sensor element constituted by an oxygen-ion conductive solid electrolyte and measures a concentration of a predetermined gas component of a measurement gas, said sensor element comprising:
   a first gas inlet communicating with the outside;
   a first internal space communicating with said first gas inlet via a predetermined diffusion control part;
   a second internal space communicating with said first internal space via a second predetermined diffusion control part;
   a third internal space communicating with said second internal space via a third predetermined diffusion control part;
   a second gas inlet causing said outside and said third internal space to directly communicate with each other;
   a sensing electrode located in said third internal space;
   a reference gas introduction space into which a reference gas is introduced;
   a reference electrode located in said reference gas introduction space;
   an oxygen pumping cell including an inside pump electrode facing said first internal space, an outside pump electrode located on an outside surface of said sensor element, and said solid electrolyte located between said inside pump electrode and said outside pump electrode; and
   a main gas distribution part being a path extending from said first gas inlet to said third internal space, wherein
   said gas sensor is configured and disposed so as to determine the concentration of said predetermined gas component contained in the measurement gas introduced from said second gas inlet into said third internal space on the basis of a potential difference between said sensing electrode and said reference electrode, while causing said oxygen pumping cell to pump oxygen in or out for said measurement gas flowing via said main gas distribution part such that an oxygen concentration of said second internal space is maintained at a constant value of 1 vol % or more, and $3.5 \leq D2/D1 \leq 6$ is satisfied, where D2/D1 is a diffusion resistance ratio, D1 is a diffusion resistance of said measurement gas flowing from an outside edge position of said first gas inlet to a position of said sensing electrode in said third internal space via said main gas distribution part, and D2 is a diffusion resistance of said measurement gas flowing from an outside edge position of said second gas inlet to said position of said sensing electrode in said third internal space.

6. The gas sensor according to claim 5, wherein said sensor element further comprises, in said second internal space, a monitor electrode for monitoring the oxygen concentration of said second internal space, and said oxygen pumping cell pumps oxygen in or out for said measurement gas flowing via said main gas distribution part on the basis of the potential difference between said monitoring electrode and said reference electrode.

7. The gas sensor according to claim 1, wherein said sensor element includes a plurality of solid electrolyte layers laminated, and said second gas inlet extends in a lamination direction of said plurality of solid electrolyte layers.

8. The gas sensor according to claim 1, wherein said sensor element includes a plurality of solid electrolyte layers laminated, and said second gas inlet extends in a direction perpendicular to a lamination direction of said plurality of solid electrolyte layers.

9. The gas sensor according to claim 5, wherein said sensor element includes a plurality of solid electrolyte layers laminated, and said second gas inlet extends in a lamination direction of said plurality of solid electrolyte layers.

10. The gas sensor according to claim 5, wherein said sensor element includes a plurality of solid electrolyte layers laminated, and said second gas inlet extends in a direction perpendicular to a lamination direction of said plurality of solid electrolyte layers.

11. A method of manufacturing mixed-potential gas sensor that includes a sensor element constituted by an oxygen-ion conductive solid electrolyte and measures a concentration of a predetermined gas component of a measurement gas, said sensor element comprising:
   a first gas inlet communicating with the outside;
   a first internal space communicating with said first gas inlet via a predetermined diffusion control part;
   a second internal space communicating with said first internal space via a second predetermined diffusion control part;
   a second gas inlet causing said outside and said second internal space to directly communicate with each other;
   a sensing electrode located in said second internal space;
   a reference gas introduction space into which a reference gas is introduced;
   a reference electrode located in said reference gas introduction space;
   an oxygen pumping cell including an inside pump electrode facing said first internal space, an outside pump electrode located on an outside surface of said sensor element, and said solid electrolyte located between said inside pump electrode and said outside pump electrode; and
   a main gas distribution part being a path extending from said first gas inlet to said second internal space, wherein
   said gas sensor is configured and disposed so as to determine the concentration of said predetermined gas component contained in the measurement gas introduced from said second gas inlet into said second internal space on the basis of the potential difference between said sensing electrode and said reference electrode, while causing said oxygen pumping cell to pump oxygen in or out for said measurement gas flowing via said main gas distribution part such that an oxygen concentration of said second internal space is maintained at a constant value of 1 vol % or more, and $3.5 \leq D2/D1 \leq 6$ is satisfied, where D2/D1 is a diffusion resistance ratio, D1 is a diffusion resistance of said measurement gas flowing from an outside edge position of said first gas inlet to a position of said sensing electrode in said second internal space via said main gas distribution part, and D2 is a diffusion resistance of said measurement gas flowing from an outside edge position of said second gas inlet to said position of said sensing electrode in said second internal space, said method comprising the steps of:
a) laminating a plurality of ceramic green sheets containing said solid electrolyte as a ceramic component to form a laminated body;
b) firing said laminated body; and
c) providing a through-hole by irradiating said laminated body obtained in said step b) with laser light to form said second gas inlet.

12. A method of manufacturing mixed-potential gas sensor that includes a sensor element constituted by an oxygen-ion conductive solid electrolyte and measures a concentration of a predetermined gas component of a measurement gas, said sensor element comprising:
   a first gas inlet communicating with the outside;
   a first internal space communicating with said first gas inlet via a predetermined diffusion control part;
   a second internal space communicating with said first internal space via a second predetermined diffusion control part;
   a second gas inlet causing said outside and said second internal space to directly communicate with each other;
   a sensing electrode located in said second internal space;
   a reference gas introduction space into which a reference gas is introduced;
   a reference electrode located in said reference gas introduction space;
   an oxygen pumping cell including an inside pump electrode facing said first internal space, an outside pump electrode located on an outside surface of said sensor element, and said solid electrolyte located between said inside pump electrode and said outside pump electrode; and
   a main gas distribution part being a path extending from said first gas inlet to said second internal space, wherein
   said gas sensor is configured and disposed so as to determine the concentration of said predetermined gas component contained in the measurement gas introduced from said second gas inlet into said second internal space on the basis of the potential difference between said sensing electrode and said reference electrode, while causing said oxygen pumping cell to pump oxygen in or out for said measurement gas flowing via said main gas distribution part such that an oxygen concentration of said second internal space is maintained at a constant value of 1 vol % or more, and 3.5≤$D2/D1$≤6 is satisfied, where $D2/D1$ is a diffusion resistance ratio, $D1$ is a diffusion resistance of said measurement gas flowing from an outside edge position of said first gas inlet to a position of said sensing electrode in said second internal space via said main gas distribution part, and $D2$ is a diffusion resistance of said measurement gas flowing from an outside edge position of said second gas inlet to said position of said sensing electrode in said second internal space, said method comprising the steps of:
a) performing punching at a position at which said second gas inlet is to be formed in a plurality of ceramic green sheets containing said solid electrolyte as a ceramic component;
b) laminating said plurality of ceramic green sheets after said step a) to form a laminated body; and
c) firing said laminated body.

13. A method of manufacturing mixed-potential gas sensor that includes a sensor element constituted by an oxygen-ion conductive solid electrolyte and measures a concentration of a predetermined gas component of a measurement gas, said sensor element comprising:
a first gas inlet communicating with the outside;
a first internal space communicating with said first gas inlet via a predetermined diffusion control part;
a second internal space communicating with said first internal space via a second predetermined diffusion control part;
a second gas inlet causing said outside and said second internal space to directly communicate with each other;
a sensing electrode located in said second internal space;
a reference gas introduction space into which a reference gas is introduced;
a reference electrode located in said reference gas introduction space;
an oxygen pumping cell including an inside pump electrode facing said first internal space, an outside pump electrode located on an outside surface of said sensor element, and said solid electrolyte located between said inside pump electrode and said outside pump electrode; and
a main gas distribution part being a path extending from said first gas inlet to said second internal space, wherein
said gas sensor is configured and disposed so as to determine the concentration of said predetermined gas component contained in the measurement gas introduced from said second gas inlet into said second internal space on the basis of the potential difference between said sensing electrode and said reference electrode, while causing said oxygen pumping cell to pump oxygen in or out for said measurement gas flowing via said main gas distribution part such that an oxygen concentration of said second internal space is maintained at a constant value of 1 vol % or more, and 3.5≤$D2/D1$≤6 is satisfied, where $D2/D1$ is a diffusion resistance ratio, $D1$ is a diffusion resistance of said measurement gas flowing from an outside edge position of said first gas inlet to a position of said sensing electrode in said second internal space via said main gas distribution part, and $D2$ is a diffusion resistance of said measurement gas flowing from an outside edge position of said second gas inlet to said position of said sensing electrode in said second internal space, said method comprising the steps of:
a) applying a decomposition material to a position at which said second gas inlet is to be formed in a plurality of ceramic green sheets containing said solid electrolyte as a ceramic component;
b) laminating said plurality of ceramic green sheets after said step a) to form a laminated body; and
c) firing said laminated body.

14. A method of manufacturing mixed-potential gas sensor that includes a sensor element constituted by an oxygen-ion conductive solid electrolyte and measures a concentration of a predetermined gas component of a measurement gas, said sensor element comprising:
a first gas inlet communicating with the outside;
a first internal space communicating with said first gas inlet via a predetermined diffusion control part;
a second internal space communicating with said first internal space via a second predetermined diffusion control part;
a third internal space communicating with said second internal space via a third predetermined diffusion control part;
a second gas inlet causing said outside and said third internal space to directly communicate with each other;
a sensing electrode located in said third internal space;
a reference gas introduction space into which a reference gas is introduced;
a reference electrode located in said reference gas introduction space;
an oxygen pumping cell including an inside pump electrode facing said first internal space, an outside pump electrode located on an outside surface of said sensor element, and said solid electrolyte located between said inside pump electrode and said outside pump electrode; and
a main gas distribution part being a path extending from said first gas inlet to said third internal space, wherein
said gas sensor is configured and disposed so as to determine the concentration of said predetermined gas component contained in the measurement gas introduced from said second gas inlet into said third internal space on the basis of the potential difference between said sensing electrode and said reference electrode, while causing said oxygen pumping cell to pump oxygen in or out for said measurement gas flowing via said main gas distribution part such that an oxygen concentration of said second internal space is maintained at a constant value of 1 vol % or more, and 3.5≤$D2/D1$≤6 is satisfied, where $D2/D1$ is a diffusion resistance ratio, $D1$ is a diffusion resistance of said measurement gas flowing from an outside edge position of said first gas inlet to a position of said sensing electrode in said third internal space via said main gas distribution part, and $D2$ is a diffusion resistance of said measurement gas flowing from an outside edge position of said second gas inlet to said position of said sensing electrode in said third internal space, said method comprising the steps of:
a) laminating a plurality of ceramic green sheets containing said solid electrolyte as a ceramic component to form a laminated body;
b) firing said laminated body; and
c) providing a through-hole by irradiating said laminated body obtained in said step b) with laser light to form said second gas inlet.

15. A method of manufacturing mixed-potential gas sensor that includes a sensor element constituted by an oxygen-ion conductive solid electrolyte and measures a concentration of a predetermined gas component of a measurement gas, said sensor element comprising:
a first gas inlet communicating with the outside;
a first internal space communicating with said first gas inlet via a predetermined diffusion control part;
a second internal space communicating with said first internal space via a second predetermined diffusion control part;
a third internal space communicating with said second internal space via a third predetermined diffusion control part;
a second gas inlet causing said outside and said third internal space to directly communicate with each other;
a sensing electrode located in said third internal space;
a reference gas introduction space into which a reference gas is introduced;
a reference electrode located in said reference gas introduction space;
an oxygen pumping cell including an inside pump electrode facing said first internal space, an outside pump electrode located on an outside surface of said sensor element, and said solid electrolyte located between said inside pump electrode and said outside pump electrode; and
a main gas distribution part being a path extending from said first gas inlet to said third internal space, wherein
said gas sensor is configured and disposed so as to determine the concentration of said predetermined gas component contained in the measurement gas introduced from said second gas inlet into said third internal space on the basis of the potential difference between said sensing electrode and said reference electrode, while causing said oxygen pumping cell to pump oxygen in or out for said measurement gas flowing via said main gas distribution part such that an oxygen concentration of said second internal space is maintained at a constant value of 1 vol % or more, and $3.5 \leq D2/D1 \leq 6$ is satisfied, where D2/D1 is a diffusion resistance ratio, D1 is a diffusion resistance of said measurement gas flowing from an outside edge position of said first gas inlet to a position of said sensing electrode in said third internal space via said main gas distribution part, and D2 is a diffusion resistance of said measurement gas flowing from an outside edge position of said second gas inlet to said position of said sensing electrode in said third internal space,
said method comprising the steps of:
a) performing punching at a position at which said second gas inlet is to be formed in a plurality of ceramic green sheets containing said solid electrolyte as a ceramic component;
b) laminating said plurality of ceramic green sheets after said step a) to form a laminated body; and
c) firing said laminated body.

16. A method of manufacturing mixed-potential gas sensor that includes a sensor element constituted by an oxygen-ion conductive solid electrolyte and measures a concentration of a predetermined gas component of a measurement gas, said sensor element comprising:
a first gas inlet communicating with the outside;
a first internal space communicating with said first gas inlet via a predetermined diffusion control part;
a second internal space communicating with said first internal space via a second predetermined diffusion control part;
a third internal space communicating with said second internal space via a third predetermined diffusion control part;
a second gas inlet causing said outside and said third internal space to directly communicate with each other;
a sensing electrode located in said third internal space;
a reference gas introduction space into which a reference gas is introduced;
a reference electrode located in said reference gas introduction space;
an oxygen pumping cell including an inside pump electrode facing said first internal space, an outside pump electrode located on an outside surface of said sensor element, and said solid electrolyte located between said inside pump electrode and said outside pump electrode; and
a main gas distribution part being a path extending from said first gas inlet to said third internal space, wherein
said gas sensor is configured and disposed so as to determine the concentration of said predetermined gas component contained in the measurement gas introduced from said second gas inlet into said third internal space on the basis of the potential difference between said sensing electrode and said reference electrode, while causing said oxygen pumping cell to pump oxygen in or out for said measurement gas flowing via said main gas distribution part such that an oxygen concentration of said second internal space is maintained at a constant value of 1 vol % or more, and $3.5 \leq D2/D1 \leq 6$ is satisfied, where D2/D1 is a diffusion resistance ratio, D1 is a diffusion resistance of said measurement gas flowing from an outside edge position of said first gas inlet to a position of said sensing electrode in said third internal space via said main gas distribution part, and D2 is a diffusion resistance of said measurement gas flowing from an outside edge position of said second gas inlet to said position of said sensing electrode in said third internal space,
said method comprising the steps of:
a) applying a decomposition material to a position at which said second gas inlet is to be formed in a plurality of ceramic green sheets containing said solid electrolyte as a ceramic component;
b) laminating said plurality of ceramic green sheets after said step a) to form a laminated body; and
c) firing said laminated body.

* * * * *